(12) United States Patent
Beaver

(10) Patent No.: US 11,790,460 B2
(45) Date of Patent: Oct. 17, 2023

(54) BLOCKCHAIN EVENT LOGGING BETWEEN COMPANIES

(71) Applicant: Verint Americas Inc., Alpharetta, GA (US)

(72) Inventor: Ian Beaver, Spokane, WA (US)

(73) Assignee: Verint Americas Inc., Alpharetta, GA (US)

( * ) Notice: Subject to any disclaimer, the term of this patent is extended or adjusted under 35 U.S.C. 154(b) by 445 days.

(21) Appl. No.: 16/843,417

(22) Filed: Apr. 8, 2020

(65) Prior Publication Data

US 2020/0327619 A1    Oct. 15, 2020

Related U.S. Application Data

(60) Provisional application No. 62/832,515, filed on Apr. 11, 2019.

(51) Int. Cl.

| | |
|---|---|
| *G06Q 40/12* | (2023.01) |
| *G06F 9/451* | (2018.01) |
| *G06F 21/60* | (2013.01) |
| *G06Q 30/016* | (2023.01) |
| *G16H 40/20* | (2018.01) |
| *G06N 5/043* | (2023.01) |
| *H04L 9/06* | (2006.01) |
| *H04L 9/30* | (2006.01) |
| *H04L 9/00* | (2022.01) |

(52) U.S. Cl.
CPC ............ *G06Q 40/12* (2013.12); *G06F 9/453* (2018.02); *G06F 21/602* (2013.01); *G06N 5/043* (2013.01); *G06Q 30/016* (2013.01); *G16H 40/20* (2018.01); *H04L 9/0637* (2013.01); *H04L 9/3073* (2013.01); *H04L 9/50* (2022.05)

(58) Field of Classification Search
CPC .............. G06Q 30/016; G06Q 10/0633; G06F 16/1837; G06F 21/602; H04L 9/0637
See application file for complete search history.

(56) References Cited

U.S. PATENT DOCUMENTS

| | | | |
|---|---|---|---|
| 9,363,378 B1 * | 6/2016 | McDaniel | H04M 3/53358 |
| 2015/0310188 A1 * | 10/2015 | Ford | H04L 63/0428 726/28 |
| 2017/0046638 A1 | 2/2017 | Chan et al. | |
| 2017/0177898 A1 * | 6/2017 | Dillenberger | G06F 21/6227 |

(Continued)

OTHER PUBLICATIONS

Thompson, Stephen. "The preservation of digital signatures on the blockchain." See Also 3 (2017). (Year: 2017).*

(Continued)

*Primary Examiner* — Carrie S Gilkey
(74) *Attorney, Agent, or Firm* — Meunier Carlin & Curfman, LLC

(57) ABSTRACT

A system and method using blockchain for monitoring and tracking service provider involvement in a transaction on behalf of a customer company. In the system and method, session information related to the transactions are encrypted using an encryption key specific to a company on whose behalf the service provider is acting. The encrypted action is signed the with a private key of a public/private key pair. The signed, encrypted action record is placed on the blockchain, which can later be accessed to review the actions on behalf of the specific company.

22 Claims, 2 Drawing Sheets

(56) References Cited

U.S. PATENT DOCUMENTS

2019/0123895 A1* 4/2019 Blake .................... H04L 67/133
2019/0258999 A1* 8/2019 Leonard ................ H04L 9/0637

OTHER PUBLICATIONS

D'Aliessi, M., "How Does the Blockchain Work?," OneZero, retrieved on Feb. 5, 2020 at https://medium.com/s/story/how-does-the-blockchain-work-98c8cd01d2ae, Jun. 1, 2016, 16 pages.

Ivan, D., "Moving Toward a Blockchain-based Method for the Secure Storage of Patient Records," retrieved on Jun. 30, 3030 at https://www.healthit.gov/sites/default/files/9-16-drew_ivan_20160804_blockchain_for_healthcare_final.pdf, 2016, 11 pages.

Lobosco, K., "Comcast changes customer name to A-hole on bill," retrieved on Feb. 5, 2020 at https://money.cnn.com/2015/01/29/news/companies/comcast-asshole-bill/index.html, Jan. 29, 2015, 5 pages.

Nakamoto, S., "Bitcoin: A Peer-to-Peer Electronic Cash System," retrieved on Jun. 30, 2020 at http://bitcoin.org/bitcoin.pdf, 2008, 9 pages.

Roy, S., et al., "$QA^{RT}$: A System for Real-Time Holistic Quality Assurance for Contact Center Dialogues," Proceedings of the Thirtieth AAAI Conference on Artificial Intelligence (AAAI-16), 2016, pp. 3768-3775.

International Search Report and Written Opinion, dated Jun. 19, 2020, received in connection with corresponding International Patent Application No. PCT/US2020/027939.

* cited by examiner

BLOCKCHAIN EVENT LOGGING BETWEEN COMPANIES

CROSS REFERENCE TO RELATED APPLICATIONS

This application is a non-provisional patent application claiming priority to Provisional Patent Application Ser. No. 62/832,515, filed Apr. 11, 2019 which is hereby incorporated by this reference in its entirety as if fully set forth herein.

BACKGROUND

Field

Embodiments of the present invention relate to systems and methods using a blockchain to allow external service providers to access data for billing without having to access or rely upon its customers or users to provide the data.

Background

In many instances, when an IVA/service helps a customer with a purchase on a website, once the customer is navigated to the shopping cart, the IVA is no longer aware of the sales outcome. This is to prevent the IVA from accessing the customer's personal information while completing the sale for security as the IVA is typically hosted in a different environment than the shopping cart application, or the company does not want to expose customer personally identifiable information (PII) to third parties such as IVA providers. Therefore, in order to count sale transactions that were assisted by an IVA associated with a user, the IVA provider is reliant on the company (i.e., its client or customer) to periodically (e.g., monthly) and manually report to the IVA provider which sales were assisted by an IVA. The company's report provides the information that the IVA provider is reliant on to generate a bill which is then provided to the company (e.g., based on transactional payments).

In another scenario, a common key performance indicator (KPI) for self-service is call deflection. As the IVA on a website or voice channel has no access to further customer contacts through other channels, an IVA provider is once again reliant on the company to pull reports from the company's internal databases and provide the IVA provider with data needed to charge the company for successful deflections (successful sales or other responses that the IVA provider should get paid or other credit or compensation for). This puts the IVA provider at a disadvantage because the must trust the quality of the company's (e.g., its client's or its customer's) reports for accurate billing. The IVA provider must also wait for the company to provide this report before the IVA provider can bill the company.

BRIEF SUMMARY OF THE DISCLOSURE

Accordingly, the present invention is directed to systems and methods using blockchain even logging between companies transactions that obviates one or more of the problems due to limitations and disadvantages of the related art.

In an aspect according to principles described herein, a computer product comprises computer executable code embodied in a non-transitory computer readable medium that, when executing on one or more computing devices performs a method of using blockchain to track actions of a first entity on behalf of a second entity. The method includes digitally encrypting an action of the first entity using a second entity-specific encryption key to generate an encrypted action; applying a second entity-unique digital private key to the encrypted action; and broadcasting the encrypted action to the blockchain.

In another aspect, the method includes digitally encrypting an action of the first entity using a second entity-specific encryption key to generate an encrypted action; applying a second entity-unique digital private key to the encrypted action; and broadcasting the encrypted action to the blockchain.

In another aspect according to principles described herein, a computer product comprises computer executable code embodied in a non-transitory computer readable medium that, when executing on one or more computing devices performs method of tracking records of actions of first entity on behalf of a second entity wherein a record of the first entity's actions are published to a blockchain. The method includes identifying a distributed ledger on the blockchain having records of the first entity on behalf of the second among records of the first entity on behalf of other entities; and decrypting the first entity's records using a second entity-specific decryption key such that only the first entity's actions for the second are decrypted from among the records in the distributed ledger.

It is to be understood that both the foregoing general description and the following detailed description are exemplary and explanatory only, and are not restrictive of the invention as claimed.

BRIEF SUMMARY OF THE DRAWINGS

The accompanying figures, which are incorporated herein and form part of the specification, illustrate systems and methods using blockchain for monitoring and tracking actions of a service provider on behalf of a customer.

Together with the description, the figures further serve to explain the principles of the systems and methods using blockchain for monitoring and tracking customer service representative actions described herein and thereby enable a person skilled in the pertinent art to make and use the systems and methods using blockchain for monitoring and tracking customer service representative actions.

DETAILED DESCRIPTION

Figure 1:
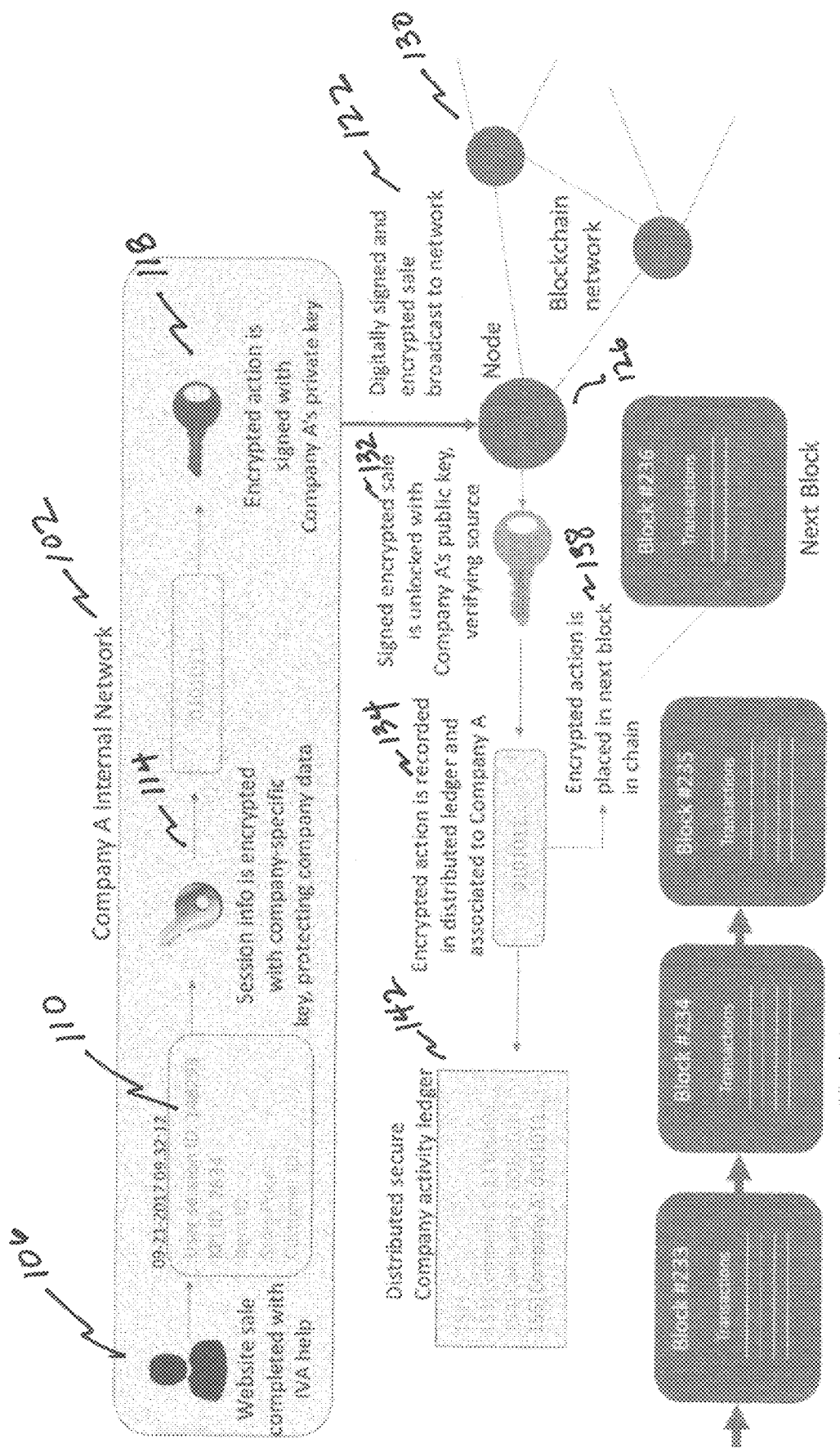
FIG. 1 illustrates recording actions and storing the service provider actions in encrypted form on the blockchain network using an intelligent virtual assistant (IVA) provider, an example service provider.

Reference will now be made in detail to embodiments of the systems and methods using a blockchain to allow intelligent virtual assistants (IVAs) reporting applications to track transactions, including sales or sensitive interactions or transactions, occurring on corporate websites or within internal environments such as a call center with reference to the accompanying figures.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The present disclosure is directed using a blockchain to allow a service provider to access data necessary for billing a customer company for services provided without having to access the data by accessing the customer company's system or having to ask the customer company for the data. Systems and methods disclosed herein may be used for products or services that may be transactional in nature and that could be deployed on site where the service provider would need access to internal data to bill accurately. An example would be data analysis tools that are billed by usage, but if the company using the data analysis tools are hosting those tools locally, the service provider not have access to that usage without access to using company's network, or intelligent virtual assistants (IVAs) reporting applications to track transactions occurring on corporate websites or within internal environments.

According to principles described herein, a company (Company A) that provides any transactional service to a second company (Company B) may access data needed to bill Company B without relying on Company B to pull reports indicating that data or for Company B to provide Company A access to Company B's network to derive the billing data on its own. For example Company A could make an agreement that every time a CSA dashboard application offers a suggestion that is followed by the CSA, Company A is due some transactional payment. Company A would need access to that data from within Company B's network in order to bill accurately as well.

In an embodiment, a blockchain contract is established for each company (i.e., each customer) and KPI. When a qualifying event takes place (e.g., a successful sale of an item, a customer contact on a new channel, etc.), it can be placed as a transaction on the blockchain with the KPI identifier and user session identifier encrypted in the payload and is signed with the company's (or customer's) key. On the Company A side, billing invoices can be automatically generated (e.g., in realtime or near-realtime) by joining the Company A session database with the public company ledger on the user session ID. Transactions can be calculated per KPI if needed. Bills can be generated faster and by transaction as the transaction is completed.

As no customer data is transmitted over the blockchain network, customer anonymity is preserved while still establishing a reliable public record of transaction that the Company A (i.e., provider) can bill against. If a dispute arises between a company and Company A (i.e., the provider), the public activity ledger on the blockchain can be consulted to settle the disagreement. Transactional data can be shared with various external sources without giving the external sources direct access to Company B's databases and/or network.

If companies do not want sales metrics publicly known, data can first be encrypted with a company specific key before sending the transaction to the network. This encryption key can be shared directly with Company A in a pre-shared key model so that Company A can decrypt the payload and calculate sales metrics. In this way, the only thing publicly known is that a company is generating transactions, but there is no public knowledge on what those transactions contain or represent.

Using an intelligent virtual assistants (IVA) as a non-limiting example of systems and methods provided herein, an IVA/service provider may use reporting applications to track transactions, including sales or sensitive interactions or transactions, occurring on corporate websites or within internal environments such as a call center. This allows the IVA/service provider to accurately track sales or interactions and thus bill clients, for example, when billing is based on call or interaction escalation metrics, e.g., when an issue is resolved at the IVA/service provider level, thus not escalating to a human interaction. The present systems and methods allow for increasing timeliness and accuracy of bills and reducing, eliminating, and/or preventing disagreements around how billing was calculated. Blockchain is used to publish transactions and for auditing. Transactions/Interactions can be published as they happen, without an IVA/service provider needing to access their client's (also known as their customer's) systems.

In an embodiment, a blockchain contract is established for each company (i.e., each customer) and KPI. When a qualifying event takes place (e.g., a successful sale of an item, a customer contact on a new channel, etc.), it can be placed as a transaction on the blockchain with the KPI identifier and user session identifier encrypted in the payload and is signed with the company's (or customer's) key. On the IVA/service provider side, billing invoices can be automatically generated (e.g., in realtime or near-realtime) by joining the IVA/service provider session database with the public company ledger on the user session ID. Transactions can be calculated per KPI if needed. Bills can be generated faster and by transaction as the transaction is completed.

As no customer data is transmitted over the blockchain network, customer anonymity is preserved while still establishing a reliable public record of transaction that the IVA/service provider can bill against. If a dispute arises between a company and the IVA/service company (i.e., the provider), the public sales activity ledger on the blockchain can be consulted to settle the disagreement. Transactional data can be shared with various external sources without giving the external sources direct access to a company's databases and/or network.

If companies do not want sales metrics publicly known, data can first be encrypted with a company specific key before sending the transaction to the network. This encryption key can be shared directly with the IVA/service company in a pre-shared key model so that the IVA/service company can decrypt the payload and calculate sales metrics. In this way, the only thing publicly known is that a company is generating transactions, but there is no public knowledge on what those transactions contain or represent.

In addition, if multiple services companies are dependent on customer transaction data, and the company does not want to reveal the same data to the different services companies, it could use multiple encryption keys to lock different parts of the transaction data so that each services company can only decrypt the attributes that pertains to their business needs. Thus, there is no need for secure connections; each company has a node on the network. Such service can include, for example, companies handling health care or patient data subject to HIPAA or other privacy requirements.

Thus, a benefit is that companies can work with external service providers in a transactional manner, such as IVA/service providers, without sharing or leaking customer data.

This innovation is relevant to any company that uses external companies to provide services where payment terms are based on customer behavior. The innovation provides a secure technique for sharing data between disconnected (e.g., external) entities. Neither party needs to open up firewalls, etc. or provide VPN access or other holes in their network to untrusted parties.

FIG. 1 illustrates placing a record of transactions on a blockchain. An IVA for Company A, for which IVA/provider services are provided by an external IVA/service provider, may have its own internal network 102. If the IVA/service provider assists a customer of company A and that assistance results in a transaction, 106, such as a sale, then the session information 110 is encrypted with an encryption key specific to Company A, 114, thus protecting the data. The session information may include various information, such as topic ID, user/customer (anonymized) ID, timestamp, etc. The session information may be customized to include whatever information is required in circumstances in which some underlying data is sought and the nature of some information means that it should not be shared. Thus, data may be shared with external entities in way for sensitive information to remain private and not inadvertently leaked. For example, the session information may include only what information is necessary to bill the IVA/service company's clients for IVA-assisted transactions.

Only certain data needs to be placed on the blockchain. For example, in the IVA example, data required for billing transactions would be placed on the blockchain. In this example, transactions in which the IVA did not assist would not be placed on the blockchain because they would not be billable to the customer. However, if the IVA provider were calculating billings based on a percentage of total transactions, then data relating to all transactions be placed on the blockchain. Such different amounts of information placed on the blockchain may vary by the type of service being provided by the service provider (Company A) and the principles described herein equally applicable.

Referring again to FIG. 1, the encrypted action is signed with Company A's company-specific encryption key 118. The digitally signed and encrypted data is broadcast to a network 122, perhaps via a node 126 of a blockchain network 130. The blockchain network 130 may be shared or private. Actions can be broadcast to the blockchain as they happen, without access to anything besides Company A's private key and the company-specific encryption key.

The signed and encrypted action may be unlocked using Company A's public key to verify the source, 132 and/or to check for sales or an IVA-assisted action. The encrypted action may be recorded in a distributed activity ledger an associated with Company A, 134. The encrypted action may be then placed on the blockchain (in addition to or in place of the prior described broadcast to the blockchain), 138. Thus, a distributed secure activity ledger of Company A's IVA-assisted actions can be maintained using the blockchain network, 142. Events may be recorded from multiple companies in a single secure Company activity ledger, such that company-specific data may coexist in the same ledger and may be extracted by company.

Figure 2:
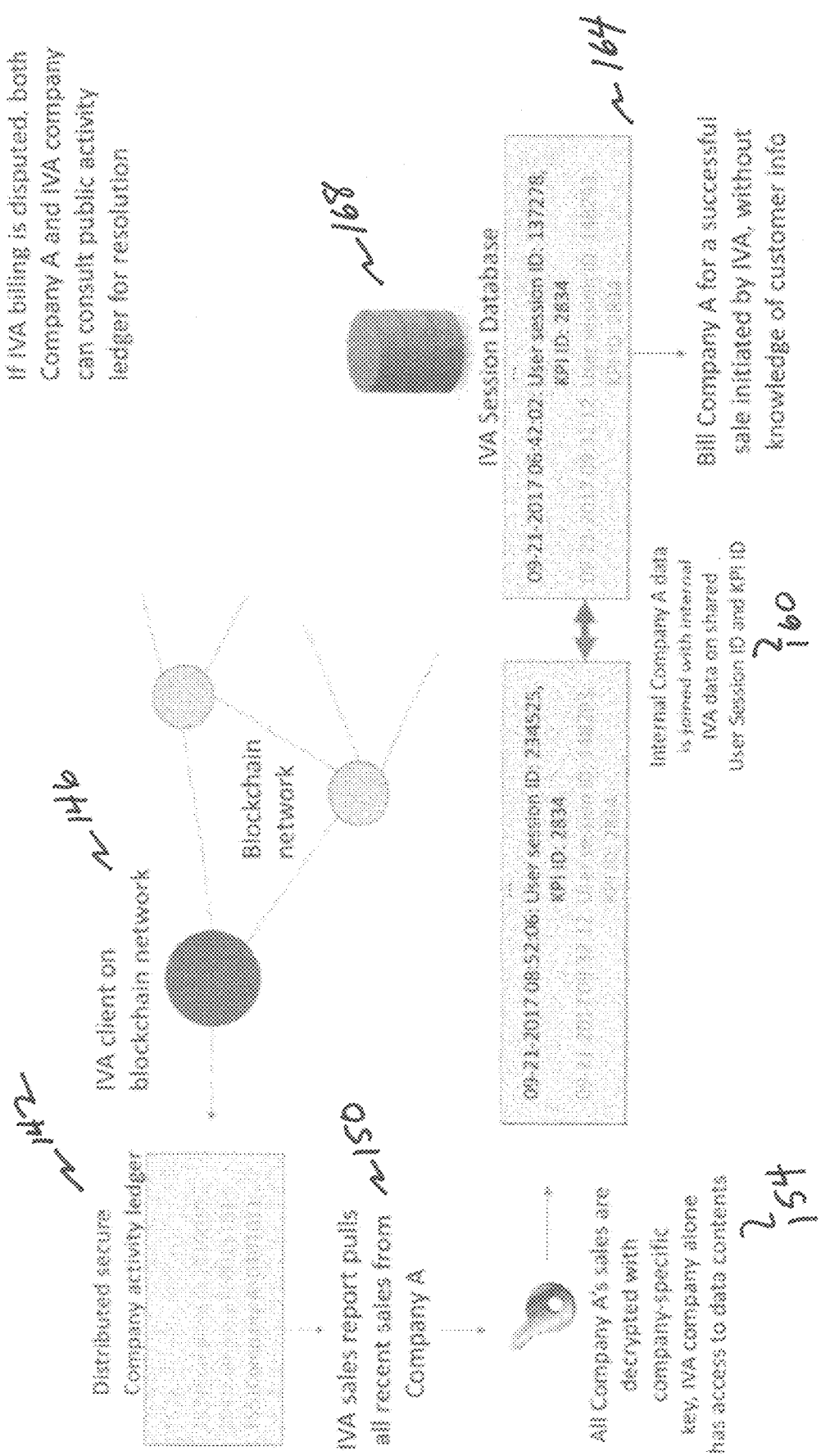
FIG. 2 illustrates how a company can audit the activities of an service provider, using an IVA provider as an example service provider.

As illustrated in FIG. 2, if IVA/service provider billing is based on interaction with Company A's customers is disputed, both Company A and the IVA/service company can consult the public activity ledger for resolution.

If Company A or the IVA/service company wants to session records in case of a dispute, the Company A or the IVA/service company only needs to run an IVA/service provider specific client on the blockchain network 146 and access the ledger of transactions 142. Using the ledger 142, an report (such as an IVA sales report) can be pulled from Company A's data in the ledger, such as all recent sales from Company A. 150. It is also possible for a Company to query all actions, e.g. pull recent data like a report of all recent sales involving IVA transactions on its behalf 150. In an aspect of the present disclosure, all Company A's data/sales may be decrypted with the pre-shared company-specific key, with the IVA/service company alone having access to the data contents 154. Internal Company A data is joined with Internal IVA/service data on a shared User Session ID and KPI ID 160. Using their company-specific key for Company A, it can then decrypt the actions and review all activities that have been performed historically for Company A by the IVA/service provider and vice versa. The record of activities is decentralized and immutable on the network preserving all actions and session details. In an aspect, a trusted key could be used to unlock all of the data in the ledger, as a way to share information.

Accordingly, using the decrypted data from the blockchain, the IVA/service company can bill Company A for successful actions/transactions on its behalf, for example, sales initiated by an IVA (e.g., with IVA assistance), without knowledge of the customer information. 164. In addition, an IVA/service provider Session Database 168 may be populated and maintained for further reference by the IVA/service company.

In the IVA example, it may be that the Company A only receives payment for its IVA customer assistance if a sale or other transaction on a website happens with the help of an IVA, e.g., the IVA makes suggestions for products or services that the customer ultimately purchases.

In accordance with principles described herein a system uses a blockchain to allow an intelligent virtual assistant (IVA)/service provider's reporting applications to track transactions, like sales, occurring on corporate websites or within internal environments such as a call center. In the system, the blockchain is used to publish transactions and/or for auditing transactions. The transactions may be published in realtime or near-realtime as they occur. Invoices based on the data on the blockchain are generated in realtime or near-realtime as the transactions are published and/or may be archived in a distributed secure activity ledger derived from the actions encrypted and published to the blockchain According to principles described herein, a method uses a blockchain to allow an IVA/service provider's reporting applications to track transactions of/for a client company. When a qualifying event takes place, the event is placed as a transaction on the blockchain with a key performance indicator (KPI) identifier and a user session identifier encrypted in the payload and is signed with a key of the company. The qualifying event may be, for example, a successful sale of an item or a customer contact on a new channel. The method may further include automatically generating an invoice by joining an IVA/service session database with a public company ledger on a user session ID. According to principles describe herein, the method allows for preserving customer anonymity while still establishing a reliable public record of transaction.

Although described above with respect to how the principles described herein are application to an IVA assisting customers of a website (Company B), the principles are application to other products that may be transactional in nature that could be deployed on site where we would need access to internal data to bill accurately. An example would be data analysis tools that billed by usage if records of the usage are hosted by the customer. The principles described herein may be, for example, provided for IVA, IVR, native mobile/desktop software applications running on-site, and server applications that are running on-site. Any software sold to a customer that may be billed transactionally that is installed locally in the customer/second entity environment will be able to use this blockchain method.

In addition to applying the principles herein in a retail support context, the present principles can be applied, for example, in a healthcare context. For example, test results or healthcare events (e.g., diagnoses) can be published to the blockchain and provided in a distributed secure activity ledger. For example, the Centers for Disease Control or hospitals or other health care providers can subscribe to the blockchain in such a way to share anonymized data, diagnoses, test results, etc. while maintaining privacy and compliance with various regulations, such as HIPAA (The Health Insurance Portability and Accountability Act of 1996).

Throughout this application, various publications may have been referenced. The disclosures of these publications in their entireties are hereby incorporated by reference into this application in order to more fully describe the state of the art to which this invention pertains.

[1] Katie Lobosco. Comcast changes customer name to a-hole on bill, Retrieved Sep. 17 2018. https://money.cnn.com/2015/01/29/news/companies/comcast-asshole-bill/index.html.
[2] Shourya Roy, Ragunathan Mariappan, Sandipan Dandapat, Saurabh Sri-vastava, Sainyam Galhotra, and Balaji Peddamuthu. Qa rt: A system for real-time holistic quality assurance for contact center dialogues. In Thirtieth AAAI Conference on Artificial Intelligence, 2016.
[3] Michele D'Aliessi. How does the blockchain work?, Retrieved Sep. 17 2018. https://medium.com/s/story/how-does-the-blockchain-work-98c8cd01d2ae.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A non-transitory computer readable medium, comprising instructions that when executed by a processing system causes the processing system to perform a method of billing a customer company of an intelligent virtual assistant (IVA) service provider based on qualifying events of the IVA service provider, the method comprising:
   identifying a qualifying event of the IVA service provider;
   digitally encrypting session information related to the qualifying event of the IVA service provider using an encryption key of the customer company to generate an encrypted action, the session information comprising session identifying information, topic, customer identification, timestamp, sales price, or item sold;
   signing the encrypted action by applying a digital private key unique to the customer company to the encrypted action;
   recording the encrypted action in a distributed ledger by broadcasting the encrypted action to the blockchain; and
   automatically generating an invoice based on the qualifying event as the encrypted action is broadcast to the blockchain;
   wherein each of the records placed in the distributed ledger by the IVA service provider has been encrypted using an IVA-specific encryption key and a customer company-specific encrypted key unique to the entity on whose behalf the IVA service provider has acted.

2. The non-transitory computer readable medium of claim 1, further comprising a software WA service provider running on a client of the customer company.

3. The non-transitory computer readable medium of claim 1, the method further comprising associating the encrypted action with the IVA service provider.

4. The non-transitory computer readable medium of claim 1, the method further comprising verifying the encrypted action originated from the IVA service provider by applying a public key associated with the digital private key unique to the customer company.

5. The non-transitory computer readable medium of claim 4, wherein the broadcasting the encrypted action to the blockchain is performed after applying the public key to the encrypted action.

6. The non-transitory computer readable medium of claim 1, wherein the encryption key of the customer company is a unique strong encryption key.

7. The non-transitory computer readable medium of claim 1, further comprising generating a distributed activity ledger comprising a plurality of the encrypted actions.

8. The non-transitory computer readable medium of claim 1, wherein the IVA service provider is a healthcare provider and the customer company is a health data collection entity.

9. The non-transitory computer readable medium of claim 1, wherein the IVA service provider is one of an intelligent virtual assistant (IVA) provider and an interactive voice response (IVR) provider and the customer company is a customer of the IVA service provider, wherein the encrypted action includes information for the IVA service provider to bill the customer company for the action.

10. A method of billing a customer company of intelligent virtual assistant (IVA) service provider based on qualifying events of the IVA service provider, the method comprising:
    identifying a qualifying event of the IVA service provider;
    digitally encrypting session information related to the qualifying event of the IVA service provider using an encryption key unique to the customer company to generate an encrypted action, the session information comprising session identifying information, topic, customer identification, timestamp, sales price, or item sold;
    signing the encrypted action by applying a digital private key unique to the customer company to the encrypted action;
    recording the encrypted action in a distributed ledger by broadcasting the encrypted action to the blockchain; and
    automatically generating an invoice based on the qualifying event as the encrypted action is broadcast to the blockchain;
    wherein each of the records placed in the distributed ledger by the IVA service provider has been encrypted using an IVA-specific encryption key and a customer company-specific encrypted key unique to the entity on whose behalf the IVA service provider has acted.

11. The method of claim 10, comprising running a software application of the WA service provider running on a client of the customer company.

12. The method of claim 10, further comprising associating the encrypted action with IVA service provider.

13. The method of claim 10, further comprising verifying the encrypted action originated from the IVA service provider by applying a public key associated with the digital private key unique to the customer company.

14. The method of claim 13, wherein the broadcasting the encrypted action to the blockchain is performed after applying the public key to the encrypted action.

15. The method of claim 10, wherein the encryption key unique to the customer company is a unique strong encryption key.

16. The method of claim 10, further comprising generating a distributed activity ledger comprising a plurality of the encrypted actions.

17. The method of claim 10, wherein the IVA service provider is a healthcare provider and the customer company is a health data collection entity.

18. The method of claim 10, wherein the IVA service provider is one of an intelligent virtual assistant (IVA) provider and an interactive voice response (IVR) provider and the customer company is a customer of the IVA service provider, wherein the encrypted action includes information for the IVA service provider to bill the customer company for the action.

19. A non-transitory computer readable medium, comprising instructions that when executed by a processing system causes the processing system to perform a method of tracking records of actions of an intelligent virtual assistant (IVA) service provider on behalf of a customer company wherein a record of the IVA service provider's actions are published to a blockchain, the method comprising:
   identifying a distributed ledger on the blockchain having records of the WA service provider on behalf of the customer company among records of the IVA service provider on behalf of other entities wherein each of the records placed in the distributed ledger by the IVA service provider has been encrypted using an IVA-specific encryption key and a customer company-specific encrypted key unique to the entity on whose behalf the IVA service provider has acted;
   decrypting the WA service provider's records using a customer company-specific decryption key such that only the IVA service provider's actions for the customer company are decrypted from among the records in the distributed ledger; and
   analyzing sales data related to the IVA service provider's actions for the customer company.

20. The non-transitory computer readable medium of claim 19, further comprising running a software application of the IVA service provider on a client of the customer company.

21. The non-transitory computer readable medium of claim 19, wherein the WA service provider is a healthcare provider and the customer company is a health data collection entity.

22. The non-transitory computer readable medium of claim 19, wherein the WA service provider is one of an intelligent virtual assistant (IVA) provider and an interactive voice response (IVR) provider and the customer company is a customer of the WA service provider, wherein the encrypted action includes information for the WA service provider to bill the customer for the action.

* * * * *